US012788833B2

(12) United States Patent
Yoshii et al.

(10) Patent No.: US 12,788,833 B2
(45) Date of Patent: Nov. 10, 2026

(54) METHOD FOR PRODUCING RADIOPHARMACEUTICAL AND RADIOPHARMACEUTICAL

(71) Applicant: National Institutes for Quantum Science and Technology, Chiba (JP)

(72) Inventors: Yukie Yoshii, Chiba (JP); Meiei Cho, Chiba (JP); Kazunori Kawamura, Chiba (JP); Hisashi Suzuki, Chiba (JP); Hiroki Hashimoto, Chiba (JP)

(73) Assignee: National Institutes for Quantum Science and Technology, Chiba (JP)

( * ) Notice: Subject to any disclaimer, the term of this patent is extended or adjusted under 35 U.S.C. 154(b) by 1303 days.

(21) Appl. No.: 17/598,400

(22) PCT Filed: Feb. 14, 2020

(86) PCT No.: PCT/JP2020/005830
§ 371 (c)(1),
(2) Date: Sep. 27, 2021

(87) PCT Pub. No.: WO2020/202831
PCT Pub. Date: Oct. 8, 2020

(65) Prior Publication Data

US 2022/0175973 A1 Jun. 9, 2022

(30) Foreign Application Priority Data

Mar. 29, 2019 (JP) ................................ 2019-068873

(51) Int. Cl.

| | |
|---|---|
| ***A61K 51/04*** | (2006.01) |
| ***A61K 47/10*** | (2017.01) |
| ***A61K 47/20*** | (2006.01) |
| ***A61K 47/22*** | (2006.01) |
| ***A61K 47/26*** | (2006.01) |

(52) U.S. Cl.
CPC .......... *A61K 51/0478* (2013.01); *A61K 47/10* (2013.01); *A61K 47/20* (2013.01); *A61K 47/22* (2013.01); *A61K 47/26* (2013.01)

(58) Field of Classification Search
CPC .... A61K 51/0478; A61K 47/10; A61K 47/20; A61K 47/22; A61K 47/26; A61K 9/08; A61K 51/121; A61P 35/00
See application file for complete search history.

(56) References Cited

U.S. PATENT DOCUMENTS

| | | | | |
|---|---|---|---|---|
| 2010/0196272 A1 | 8/2010 | Magneson et al. | | |
| 2014/0186260 A1* | 7/2014 | Yoshii ................ | A61K 51/0478 424/1.65 | |
| 2015/0056136 A1 | 2/2015 | Cesati et al. | | |

FOREIGN PATENT DOCUMENTS

| | | | | |
|---|---|---|---|---|
| JP | H08245425 A | 9/1996 | | |
| JP | 2006528644 A | 12/2006 | | |
| JP | 2012514007 A | 6/2012 | | |
| JP | 2012524064 A | 10/2012 | | |
| JP | 2014129316 A | 7/2014 | | |
| JP | 2015516457 A | 6/2015 | | |
| JP | 2016515517 A | 5/2016 | | |
| JP | 2016528233 A | 9/2016 | | |
| JP | 6085810 B2 | 3/2017 | | |
| JP | 2017190354 A | 10/2017 | | |
| WO | WO-2007056205 A2 * | 5/2007 | ............ A61K 9/141 | |
| WO | 2011076825 A1 | 6/2011 | | |
| WO | WO-2011147762 A2 * | 12/2011 | ........... A61K 51/121 | |

OTHER PUBLICATIONS

H. M. Talaat et al., Radiochemistry, Synthesis of 99mTc-Radiolabeled Uridine as a Potential Tumor Imaging Agent, 2018, 60, 51-57 (Year: 2018).*
Matsumoto et al., Journal of Radioanalytical and Nuclear Chemistry, Process development of [64Cu]Cu-ATSM: efficient stabilization and sterilization for therapeutic applications, 2019, 322, 467-475 (Year: 2019).*
H. M. Talaat et al., Radiochemistry, Synthesis of 99mTc-Radiolabeled Uridine as a Potential Tumor Imaging Agent, 2018, 60, 51-57 (Year: 2018) (Year: 2018).*
Talaat (Radiochemistry, Synthesis of 99mTc-Radiolabeled Uridine as a Potential Tumor Imaging Agent, 2018, 60, 51-57) (Year: 2018).*
Chinese Patent Office, Office Action issued in CN 202080025813.X dated Nov. 28, 2022.
Scott et al, Studies into radiolytic decomposition of fluorine-18 labeled radiopharmaceuticals for positron emission tomography, Appl. Radiat. Isot., 2009, vol. 67, pp. 88-94.
Chen et al, Synthesis, stabilization and formulation of [177Lu]Lu-AMBA, a systemic radiotherapeutic agent for Gastrin Releasing Peptide receptor positive tumors, Appl. Radiat. Isot., 2008, vol. 66, pp. 497-505.
Mohsin et al., Comparison of Stabilizers, Myo-Inositol and D-Mannitol for 99mTc-DMSA (III), J. Chem. Soc. Pak., 2008, vol. 30, No. 6, pp. 907-912.

(Continued)

*Primary Examiner* — Jake M Vu
*Assistant Examiner* — Samantha L Mejias
(74) *Attorney, Agent, or Firm* — Wood Herron & Evans LLP

(57) ABSTRACT

A method for producing a radiopharmaceutical, the method capable of maintaining a radioactive compound retaining a chemical structure and radioactivity at the time of production and after the production, and maintaining a usable period of a radiopharmaceutical; and a radiopharmaceutical are provided. The method for producing a radiopharmaceutical that has a radioactive component containing a radioactive dithiosemicarbazone copper complex includes: a stabilization step of adding a stabilizing agent containing at least one compound selected from the group consisting of ascorbic acid, methionine, sodium ascorbate, mannitol, and butylhydroxyanisole to a solution containing the radioactive component; and a filtration step of filtering the solution containing the radioactive component or a precursor thereof with a sterilization filter. In the radiopharmaceutical, a concentration of the radioactive component is 200 MBq/mL or more in terms of radioactivity concentrations.

13 Claims, 8 Drawing Sheets

(56) References Cited

OTHER PUBLICATIONS

Talaat et al., Synthesis of 99mTc-Radiolabeled Uridine as a Potential Tumor Imaging Agent, Radiochemistry, 2018, vol. 60, No. 1 pp. 51-57.
PCT Office, International Search Report issued in PCT/JP2020/005830 mailed on Apr. 14, 2020.

* cited by examiner

METHOD FOR PRODUCING RADIOPHARMACEUTICAL AND RADIOPHARMACEUTICAL

TECHNICAL FIELD

The present invention relates to a radiopharmaceutical, and a method for producing the same.

BACKGROUND ART

Radioactive dithiosemicarbazone copper complexes have been conventionally known as a diagnostic agent for hypoxic sites and mitochondrial dysfunction and studies on their administration into a body have been conducted (for example, Patent Literature 1).

In Japan, cancer is the leading cause of death, and there is no effective treatment method for refractory cancers. Until now, it has been reported that tumors in a hypoxia lead to resistance to radiation and anticancer drugs in many refractory cancers. It is known that, among the above-mentioned radioactive copper complex compounds, a radioactive diacetyl-bis(N4-methylthiosemicarbazone) copper complex (hereinafter referred to as "Cu-ATSM"). For example, $^{64}$Cu-ATSM accumulates within tumors in environments of hypoxia, emits β-rays and Auger electrons suitable for treating tumors, and thus has a high therapeutic effect on refractory cancers, and research is carried out to put it to practical use as a therapeutic agent for cancer.

For example, Patent Literature 2 by the inventors of the present invention discloses a radiopharmaceutical and pharmaceutical kit, which is used for co-administration with a chelating agent and contains Cu-ATSM. The chelating agent contains a polydentate ligand having a maximum number of conformations of 2 to 4. This technique can promote excretion of radioactivity from the liver by using Cu-ATSM as a radiopharmaceutical for therapeutic purposes, and using a radioactive dithiosemicarbazone copper complex and a specific chelating agent in combination. And thus it aims at reducing exposure of the liver to radiation during administration of the radioactive dithiosemicarbazone copper complex.

CITATION LIST

Patent Literature

[Patent Literature 1]
Japanese Unexamined Patent Application, First Publication No. H8-245425
[Patent Literature 2]
Japanese Patent No. 6085810

SUMMARY OF INVENTION

Technical Problem

In order for it to exhibit efficacy of cancer treatment, it is needed for a radiopharmaceutical to emit high-quality and sufficient intensity and quantity of β-rays and Auger electrons, within a predetermined time in the body For this reason, it is desirable that the radiopharmaceutical be formulated at a concentration of at least 200 MBq/mL which is higher than 100 MBq/mL or less that is a radioactivity concentration used as a conventional diagnostic agent. In a case where a drug having such a high radioactivity concentration is handled, it must be produced as safely as possible and at a high recovery percentage in order to sufficiently ensure safety and efficiency in a preparation.

In addition, radioactivity of radioactive substances decreases with time, but there is a case where radioactively labeled compounds are denatured by the influence of radiation. Cu-ATSM is unstable in an aqueous solution due to radiolysis. For example, in the case of $^{64}$Cu-ATSM, there is a problem that it cannot be stored and must be used immediately after production. However, as a production process and storage conditions after the production, it is required to maintain a period during which the $^{64}$Cu-ATSM can be used without being denatured in a medical facility while maintaining a high radioactivity concentration, a quality thereof, that is, radiochemical purity.

For radiopharmaceuticals, there is a need for a stable production technology that can achieve sufficient compatibility of maintaining a high recovery percentage during production while maintaining a radioactivity concentration of radioactively labeled active ingredients and maintaining a radioactivity concentration of the active ingredients at the time of production and after the production.

The present invention has been made in view of the above circumstances, and an object thereof is to provide a method for producing a radiopharmaceutical, the method capable of maintaining a radioactive compound retaining a chemical structure and radioactivity at the time of production and after the production, and maintaining a usable period of a radiopharmaceutical; and a radiopharmaceutical.

Solution to Problem

In order to solve the above problems, the present invention has the following aspects.

[1] A method for producing a radiopharmaceutical that includes a radioactive component containing a radioactive dithiosemicarbazone copper complex represented by General Formula (1), the method including:

a stabilization step of adding a stabilizing agent containing at least one compound selected from the group consisting of ascorbic acid, methionine, sodium ascorbate, mannitol, and butylhydroxyanisole to a solution containing the radioactive component; and a filtration step of filtering the solution containing the radioactive component or a precursor thereof with a sterilization filter, in which, in the radiopharmaceutical, a concentration of the radioactive component is 200 MBq/mL or more in terms of radioactivity concentrations.

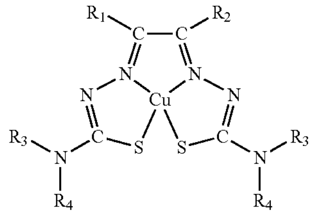

(1)

(in the formula, $R_1$, $R_2$, $R_3$, and $R_4$ each independently represent a hydrogen atom, an alkyl group, or an alkoxy group; and Cu represents a radioactive isotope of copper.)

[2] The method for producing a radiopharmaceutical according to [1], in which, in the filtration step, a filter having hydrophilic PVDF as a constituent material is used as the sterilization filter.

[3] The method for producing a radiopharmaceutical according to [1] or [2], in which, in the stabilization step, the stabilizing agent contains at least one compound selected from the group consisting of ascorbic acid, sodium ascorbate, and mannitol.

[4] The method for producing a radiopharmaceutical according to any one of [1] to [3], in which, in the radiopharmaceutical, a concentration of the radioactive component is 1 GBq/mL or more in terms of radioactivity concentrations.

[5] A radiopharmaceutical including:

a radioactive component containing a radioactive dithiosemicarbazone copper complex represented by General Formula (1); and a stabilizing agent containing at least one compound selected from the group consisting of ascorbic acid, methionine, sodium ascorbate, mannitol, and butylhydroxyanisole, in which a concentration of the radioactive component is 200 MBq/mL or more in terms of radioactivity concentrations.

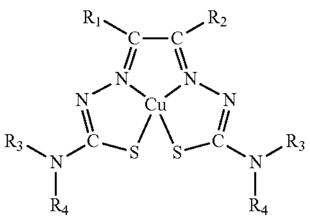

(1)

(in the formula, $R_1$, $R_2$, $R_3$, and $R_4$ each independently represent a hydrogen atom, an alkyl group, or an alkoxy group; and Cu represents a radioactive isotope of copper.)

[6] The radiopharmaceutical according to [5], in which the stabilizing agent contains at least one compound selected from the group consisting of ascorbic acid, sodium ascorbate, and mannitol.

[7] The radiopharmaceutical according to [5] or [6], in which a concentration of the radioactive component is 1 GBq/mL or more in terms of radioactivity concentrations.

[8] The radiopharmaceutical according to any one of [5] to [7], in which the radioactive component is a fraction filtered with a sterilization filter.

[9] The radiopharmaceutical according to [8], in which the fraction is a fraction filtered with the sterilization filter having hydrophilic PVDF as a constituent material.

[10] The radiopharmaceutical according to any one of [5] to [9], in which the radiopharmaceutical is a therapeutic agent or an imaging agent for tumors.

Advantageous Effects of Invention

According to the present invention, a method for producing a radiopharmaceutical, the method capable of maintaining a radioactive compound retaining a chemical structure and radioactivity at the time of production and after the production, and maintaining a usable period of a radiopharmaceutical; and a radiopharmaceutical are obtained.

DESCRIPTION OF EMBODIMENTS

Figure 1:
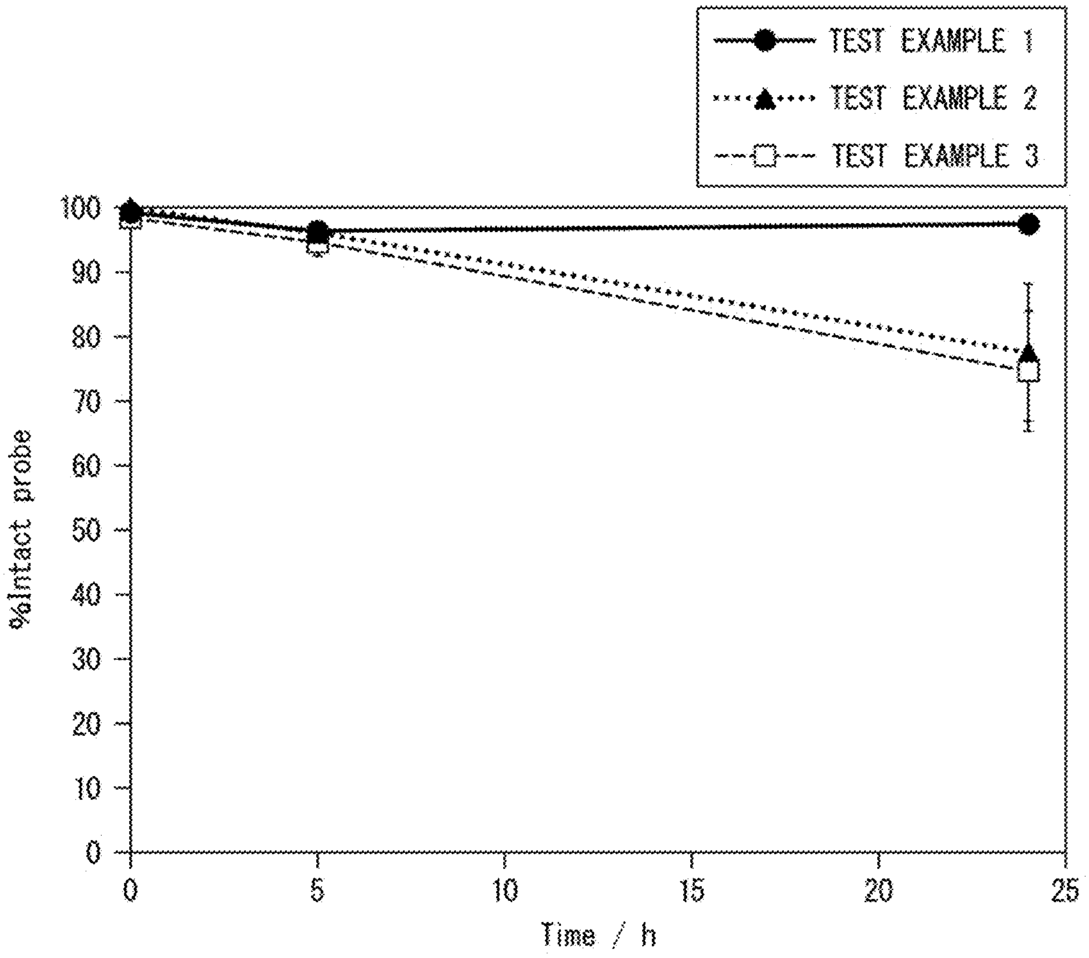
FIG. 1 is a graph showing a radiochemical purity of an acid-based candidate compound for a stabilizing agent on an hour basis in a present example.

Hereinafter, a method for producing a radiopharmaceutical and a radiopharmaceutical according to the present invention will be described with reference to embodiments. However, the present invention is not limited to the following embodiments.

Method for Producing Radiopharmaceutical

A method for producing a radiopharmaceutical of the present embodiment is a method for producing a radiopharmaceutical that includes a radioactive component containing a specific radioactive dithiosemicarbazone copper complex, and the method includes a stabilization step and a filtration step.

Radioactive Component

The radioactive dithiosemicarbazone copper complex of the present embodiment contains the radioactive component containing the radioactive dithiosemicarbazone copper complex represented by General Formula (1).

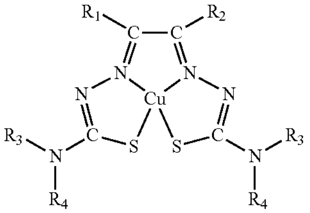

(1)

In Formula (1), $R_1$, $R_2$, $R_3$, and $R_4$ each independently represent a hydrogen atom, an alkyl group, or an alkoxy group. Cu represents a radioactive isotope of copper.

More specifically, in the present embodiment, the carbon number of an alkyl group and an alkoxy group of the substituents $R_1$, $R_2$, $R_3$, and $R_4$ in General Formula (1) is preferably an integer of 1 to 5 and is more preferably an integer of 1 to 3. In the present invention, it is preferable that the substituents $R_1$, $R_2$, $R_3$, and $R_4$ in General Formula (1) be the same as or different from each other and be a hydrogen atom or an alkyl group having 1 to 3 carbon atoms; it is more preferable that the substituents $R_1$ and $R_2$ be the same as or different from each other and be a hydrogen atom or an alkyl group having 1 to 3 carbon atoms, $R_3$ be a hydrogen atom, and $R_4$ be an alkyl group having 1 to 3 carbon atoms; and it is even more preferable that the substituents $R_1$ and $R_2$ be the same as or different from each other and be a hydrogen atom or a methyl group, $R_3$ be a hydrogen atom, and $R_4$ be a methyl group.

As the radioactive dithiosemicarbazone copper complex represented by General Formula (1), specifically, it is possible to use the following:

a radioactive glyoxal-bis(N4-methylthiosemicarbazone) copper complex,
a radioactive glyoxal-bis(N4-dimethylthiosemicarbazone) copper complex,
a radioactive ethyl glyoxal-bis(N4-methylthiosemicarbazone) copper complex,
a radioactive ethyl glyoxal-bis(N4-ethylthiosemicarbazone) copper complex,
a radioactive pyruvaldehyde-bis(N4-methylthiosemicarbazone) copper complex,
a radioactive pyruvaldehyde-bis(N4-dimethylthiosemicarbazone) copper complex,
a radioactive pyruvaldehyde-bis(N4-ethylthiosemicarbazone) copper complex,
a radioactive diacetyl-bis(N4-methylthiosemicarbazone) copper complex,
a radioactive diacetyl-bis(N4-dimethylthiosemicarbazone) copper complex,
a radioactive diacetyl-bis(N4-ethylthiosemicarbazone) copper complex, and the like.

Among them, the radioactive diacetyl-bis(N4-methylthiosemicarbazone) copper complex (hereinafter also referred to as radioactive Cu-ATSM) or the radioactive pyruvaldehyde-bis(N4-dimethylthiosemicarbazone) copper complex (hereinafter also referred to as radioactive Cu-PTSM) are preferable, and the radioactive diacetyl-bis(N4-methylthiosemicarbazone) copper complex is more preferable.

The radioactive isotope of copper in General Formula (1) is preferably $^{61}$Cu, $^{62}$Cu, $^{64}$Cu, or $^{67}$Cu, $^{61}$Cu, $^{62}$Cu, and $^{64}$Cu all emit positrons. In addition, the radioactive dithiosemicarbazone copper complexes accumulate in a hypoxic area, and among them, Cu-ATSM accumulates in cancer stem cells. For this reason, a radiopharmaceutical containing $^{61}$Cu, $^{62}$Cu, $^{64}$Cu can be used as an imaging agent for tumors or ischemia, preferably for tumors, which is used in a positron emission tomography (PET). Meanwhile, $^{64}$Cu and $^{67}$Cu also emit β-rays having a short range and have a therapeutic effect of cell disintegration. Accordingly, a radiopharmaceutical containing $^{64}$Cu or $^{67}$Cu is more preferable as a therapeutic agent for tumors.

In the present embodiment, the radioactive component is prepared before the stabilization step to be described later. For the preparation of the radioactive component, a method known so far that can prepare the compound of General Formula (1) may be appropriately used. Specifically, an organic compound that is used as a precursor of the above-mentioned radioactive component and a radioactive isotope of copper can be synthesized to prepare the radioactive component.

As the organic compound that is used as a precursor of the radioactive component, a dithiosemicarbazone derivative can be used.

As a specific production process of the organic compound that is used as a precursor, for example, a dithiosemicarbazone derivative used as a precursor of the radioactive component is synthesized according to a method described in Petering et al. (Cancer Res., 24, 367-372, 1964). That is, a 1 mol aqueous solution of α-ketoaldehyde or a 50% by volume ethanol solution is added dropwise to a 5% glacial acetic acid solution containing 2.2 mol of a precursor such as thiosemicarbazide, N4-methylthiosemicarbazide, or N4-dimethylthiosemicarbazide over 30 to 40 minutes at 50 °C to 60 °C. A reaction solution is stiffed during the dropwise addition. After completion of the dropwise addition, the mixture is left to stand at room temperature for several hours, and then is cooled to separate crystals. The crystals are dissolved in methanol and recrystallized for purification.

Subsequently, radioactive copper ions are produced. In the production of radioactive copper ions, a conventionally known production method can be used. For example, $^{61}$Cu ions can be obtained by generating $^{61}$Cu from a $^{59}$Co(α,2n)$^{61}$Cu reaction, a $^{nat}$Zn(p,x)$^{61}$Cu reaction, a $^{58}$Ni(α,p)$^{61}$Cu reaction, or the like, and thereafter, chemically separating it from a target using an ion chromatography or the like. In addition, $^{62}$Cu ions can be obtained from a $^{62}$Zn/$^{62}$Cu generator as described in, for example, WO2005/084168, Journal of Nuclear Medicine, vol. 30, 1989, pp. 1838-1842. $^{64}$Cu ions can be obtained by, for example, a method of McCarthy et al. (Nuclear Medicine and Biology, vol. 24 (1), 1997, pp. 35-43), or a method of Obata et al. (Nuclear Medicine and Biology, vol. 30 (5), 2003, pp. 535-539). $^{67}$Cu ions can be obtained by, for example, generating $^{67}$Cu from a $^{68}$Zn(p,2p)$^{67}$Cu reaction, and thereafter, chemically separating it from a target using an ion chromatography or the like.

Thereafter, the dithiosemicarbazone derivative is brought into contact with a solution containing the radioactive copper ion as a dimethyl sulfoxide (DMSO) solution. Thereby, the radioactive dithiosemicarbazone copper complex represented by General Formula (1) can be obtained. As a method for producing $^{62}$Cu-dithiosemicarbazone copper complex, a conventionally known production method can be used, and examples thereof include a method disclosed in Patent Literature 1. In addition, examples of methods for producing $^{61}$Cu-ATSM include a method of Jallian et al. (Acta Pharmaceutica, 59 (1), 2009, pp. 45-55). Examples of methods for producing $^{62}$Cu-ATSM include a method described in "Production and quality control of radiopharmaceuticals for PET: a guide to synthesis and clinical use" (PET chemistry workshop), 4th edition (revised version in 2011). Examples of methods for producing $^{64}$Cu-ATSM include a method of Tanaka et al. (Nuclear Medicine and Biology, vol. 33, 2006, pp. 743-50).

In the present embodiment, the radioactive component of the radioactive dithiosemicarbazone copper complex thus produced is made into a form of a solution containing the radioactive component before the stabilization step to be described later. The radioactive component can be made into a solution by adjusting a radioactivity concentration of a DMSO solution at the time of production. Alternatively, the radioactive component can be made into a solution by, for example, dissolving, suspending, or emulsifying the radioactive component in an aqueous solvent (water, an aqueous solution) or an oily solvent (an organic solvent).

Stabilization Step

The stabilization step is a step of adding a stabilizing agent to the above-described solution containing the radioactive component. The stabilizing agent is a component that prevents denaturation of a radioactive component to stabilize it. It is known that after a radioactive component is radiolabeling, it is denatured due to oxidation and autoradiolysis. In contrast, in the present embodiment, a radioactive component is maintained for a long time while it retains its chemical structure and radioactivity by adding the stabilizing agent.

Specifically, in the case of the $^{64}$Cu-dithiosemicarbazone copper complex conventionally used as a radioactive component, radioactivity of $^{64}$Cu is reduced by half in about 12.7 hours. In addition, the radioactive component itself is denatured with the lapse of time after production in the related art. In other words, an amount of the radioactive component, which retains its chemical structure, contained in a radiopharmaceutical decreases with the lapse of time after production, and its radioactivity decreases. The stabilizing agent is added for the purpose of inhibiting denaturation of a radioactive component, and maintaining the radioactive component while it retains its the chemical structure and radioactivity.

Effects of stabilization can be checked using, as a standard, a value obtained by measuring a percentage of % Intact probe (amount of radioactivity of radioactive component/total radioactivity×100) of radioactive components that have not been decomposed after a certain period of time after preparation (production). In the radiopharmaceutical to which the stabilizing agent is added, % Intact probe of the stabilizing agent of the present embodiment at 24 hours from preparation of a solution of a radioactive component is preferably 95% or more and is more preferably 97% or more.

In the present embodiment, a so-called radical scavenger is used as a stabilizing agent. The radical scavenger is a compound that reacts with free radicals to stabilize compounds. In general, radical scavengers are known to prevent denaturation of drugs containing radioactive compounds.

In the present embodiment, among these radical scavengers as the stabilizing agents, it is possible to use at least one compound selected from the group consisting of ascorbic acid, methionine, sodium ascorbate, mannitol, and butylhydroxyanisole. These compounds have a particularly high stabilizing effect on the radioactive component of the present embodiment, and thus can maintain the radioactive component for a long time.

In addition, in the present embodiment, it is more preferable to use ascorbic acid, sodium ascorbate, or mannitol as the stabilizing agent. Since these compounds themselves do not have carcinogenicity or the like, they can be suitably used as compounds to be contained in therapeutic agents, particularly therapeutic agents for tumors. Furthermore, since these compounds do not have odor or the like and thus are easy to handle, they can be suitably used at the time of producing and using therapeutic agents.

In a case where ascorbic acid, sodium ascorbate, or mannitol is used, an amount of the stabilizing agent added is preferably respectively 15.49 mg to 1.5 g, 0.44 mg to 44 mg, and 8.96 mg to 896 mg per 1 mL of a drug. In particular, in a case where ascorbic acid, sodium ascorbate, or mannitol is used, an amount added is more preferably respectively 154.9 mg, 4.4 mg, or 89.6 mg per 1 mL of a drug.

As effects of the stabilizing agent, as described above, the stabilizing agent inhibits denaturation of a radioactive component, and maintains the radioactive component while it retains its the chemical structure and radioactivity. An amount of the radioactive component, which retains its chemical structure, contained in a radiopharmaceutical decreases with the lapse of time after production, and its radioactivity decreases. For this reason, the $^{64}$Cu-ATSM produced in the related art could not be stored and had to be used immediately after production. It is desirable that radiopharmaceutical drugs for therapeutic purposes have a radioactivity concentration higher than that of drugs for imaging purposes which are generally mainly used in the related art in order to achieve a sufficient therapeutic effect. Accordingly, a long time was required in some cases to produce radiopharmaceuticals of the related art as to be described later, and it was difficult to exhibit a desirable medical effect unless they were used immediately after the production. It is conceivable to increase a radioactivity concentration during a production process so that a high radioactivity concentration remains even after a long time from the production, but in such a case, it is necessary to consider more safety in a production process.

In contrast, in the present embodiment, by adding the stabilizing agent to the radiopharmaceutical, the radiopharmaceutical can be maintained for a long time while retaining a chemical structure and radioactivity of the radioactive component. Therefore, it is possible to obtain a radiopharmaceutical which is easily produced because it does not have to be produced at an extremely high radioactivity concentration more than required for treatment, and which is capable of exhibiting a medical effect even after a lapse of time after the production.

Filtration Step

The filtration step is a step of filtering a radioactive component or a precursor thereof with a sterilization filter. The radiopharmaceutical is sterilized through the filtration step and thus can be used safely for administration to a human body. The radioactive component contained in the radiopharmaceutical is sterilized by filtering a precursor before synthesizing the radioactive component or a synthesized radioactive component.

In one aspect of the present embodiment, a solution to which each component of the radiopharmaceutical is added is filtered with the sterilization filter. Specifically, it is possible to filter a solution obtained by adding the stabilizing agent to a solution containing the radioactive component.

As the sterilization filter, it is possible to appropriately use sterilization filters that have been used for the conventional sterilization, specifically, a sterilization filter having a filtration size and physical properties that do not allow bacteria to pass through. For example, it is possible to use a filter made of cellulose mixed ester, or a filter having hydrophilic PES or hydrophilic PVDF as a constituent material. More specifically, regarding a filtration size of a filter, it is possible to use a filter having a pore size of 0.22 μM or less. Furthermore, a housing volume of a filter is desirably less than 10% of a total liquid volume to be filtered.

In the present embodiment, in the step of sterilizing a component containing a radioactive component, it is preferable to use the sterilization filter having hydrophilic PVDF as a constituent material among the above-mentioned sterilization filters. The step of sterilizing a component containing a radioactive component means, a step of sterilizing: a radiopharmaceutical containing a radioactive component, or a solution containing a radioactive component or a solution containing a precursor thereof, in a process of producing a radiopharmaceutical. Specifically, in a case of filtering a radiopharmaceutical containing a radioactive component, a DMSO solution of a dithiosemicarbazone derivative, or DMSO to be added to a dithiosemicarbazone derivative, it is preferable to use the sterilization filter containing hydrophilic PVDF as a constituent material.

The sterilization filter having hydrophilic PVDF as a constituent material has little absorption of the radioactive component of the present embodiment and an organic compound that is used as its precursor. Accordingly, in a case of using hydrophilic PVDF for the sterilization filter, a loss in the filtration step is small, and a high yield can be obtained during production.

As a filtration step in another aspect of the production method of the present embodiment, all of liquid components to be added to the radiopharmaceutical may be added after subjecting the respective liquid components to the filtration step. Specifically, by using fractions obtained by subjecting to filtrations of respective liquid components of any of a precursor for synthesizing the above-described radioactive component, radioactive copper, a stabilizing agent, a solution before adding these substances, or a solution after adding these substances. And all liquid components to be added to the radiopharmaceutical can become liquid components that have been subjected to the filtration step. In the above-mentioned embodiment, fractions obtained by filtering dimethyl sulfoxide to be added to the dithiosemicarbazone derivative, and an aqueous glycine solution to be added to a radioactive isotope of copper are used. In addition, also for the stabilizing agent in the above-described stabilization step, filtered fractions thereof are used. Regarding components other than the solution, components handled under sterile conditions are used. In the above-described embodiment, all components contained in the radiopharmaceutical can be sterilized by being subjected to these steps.

Regarding effects of the filtration step, a loss due to a filtration step is large and a production yield is low in a production step of the related art, because a dithiosemicarbazone copper complex is highly lipophilic and is generally easily adsorbed on a filter. For example, in the production step of the related art, in a case where such a filtration operation is performed on a solution containing a synthesized radioactive component, a large loss of a compound labeled with a radioactive substance occurs due to adsorption, and therefore production efficiency is low and an amount of waste is large. For this reason, in the production of the related art, for example, production was sometimes performed using an excessive amount of raw materials. However, in the case where an excessive amount of raw materials is used, a large amount of radioactive materials needs to be handled. Accordingly, when such a means is used, there is a problem from the viewpoint of preventing workers from radiation exposure in a production process.

In addition, in the case of the production of the related art, there is a case in which the production is performed by mixing raw materials with each other which have been subjected to sterile filtration under a sterile environment, and there are provided for production of a radioactive component using a precursor that has been filtered in advance. This production method requires many steps and may take a long time. Furthermore, in the case where many steps are required and thus a long time is taken, problems occurs from the viewpoint of not only a production yield but also exposure of workers. Since it is difficult to ensure a sufficient distance and shielding from radioactive substances in a sterile environment, it is necessary to reduce time and steps required for production as much as possible.

On the other hand, in the present embodiment, since the filtration step is performed using a filter having little adsorption of the radioactive component of the present embodiment and a precursor thereof, a loss is small and thus a production yield is high. Accordingly, it is also possible to efficiently perform a step of filtering a precursor of a radioactive component of the related art. In addition, since a loss is small even after filtering the radioactive component after production, after performing a step of producing the radioactive component and adding a stabilizing agent, it is possible to perform a filtration step on a solution containing the radioactive component and the stabilizing agent. By performing such a filtration step, the number of filtration steps is small and the number of steps is small, and thus less time is taken. Therefore, a production yield can be improved, and exposure of workers can also be ameliorated.

Other Steps

Other steps can be added to the method for producing a radiopharmaceutical of the present embodiment as needed. For example, a step of adding other components can be added. Regarding other components, for example, a component for formulating a radiopharmaceutical can be added after adding all of the above-mentioned components. The radiopharmaceutical can be formulated into an injection by adding additives such as dispersing agents, preservatives, isotonizing agents, solubilizing agents, suspending agents, buffering agents, stabilizing agents, soothing agents, or preservatives.

It is sufficient for the radiopharmaceutical of the present invention be formulated with components themselves having undergone the above-described steps, or together with a pharmacologically acceptable carrier, a diluent, or an excipient. A dosage form may be any of oral administration or parenteral administration, but a dosage form of a parenteral administration such as an injection is preferable.

Radioactivity Concentration

In the radiopharmaceutical prepared as above, a concentration of the above-described radioactive component is 200 MBq/mL or more in terms of radioactivity concentrations. A radiopharmaceutical having a high radioactivity concentration enables effective obtainment of a therapeutic effect by radiation, particularly in a case where it is used for treatment. In addition, in the radiopharmaceutical of the present embodiment, a concentration of the above-described radioactive component is more preferably 1.0 GBq/mL or more. Furthermore, for therapeutic purposes, it can be used at 1.5 GBq/mL or more. Conventional medical drugs containing radioactive components are mainly used for testing purposes, and a concentration of the radioactive components is mainly around 100 MBq/mL. However, in the present embodiment, it is possible to produce a radiopharmaceutical having a high radioactivity concentration with high efficiency. Therefore, it can be effectively used as a therapeutic agent.

Effect of Method for Producing Radiopharmaceutical of Present Embodiment

According to the method for producing a radiopharmaceutical of the present embodiment, a state in which the radioactive component is maintained without being decomposed can be maintained for a long time by the above-described stabilization step. In addition, since the filter has little adsorption of the radioactive component by the above-described filtration step, it is possible to perform sterilization without decreasing a yield of the radioactive component. According to these effects, a radiopharmaceutical can be produced and stored while stabilizing the radioactive component but not decreasing a yield thereof. Accordingly, a total of a storage time and a production time can be reduced, and a radiopharmaceutical containing a high concentration of a radioactive component can be produced in a shorter time. By using these steps in the production of radiopharmaceuticals for therapeutic use which have a high radioactivity concentration of 200 MBq/mL or more, it is possible to effectively obtain a high concentration of radioactive components and reduce a risk of exposure during the production. Thereby, a production time and costs can be greatly reduced. In addition, since the radioactive component after production is less denatured, it can be effectively used for a long time after production and is suitable as a therapeutic agent requiring transportation and storage.

Radiopharmaceutical of Present Embodiment and Use Applications Thereof

The radiopharmaceutical of the present embodiment is produced by the above-described production method. Specifically, it is the radiopharmaceutical which includes the radioactive component containing the radioactive dithiosemicarbazone copper complex represented by General Formula (1), and includes the stabilizing agent containing at least one compound selected from the group consisting of ascorbic acid, methionine, sodium ascorbate, mannitol, and butylhydroxyanisole, in which a concentration of the radioactive component is 200 MBq/mL or more in terms of radioactivity concentrations. Furthermore, the radiopharmaceutical of the present embodiment includes fractions obtained by filtering a solution containing the radioactive component and the stabilizing agent with the sterilization filter.

The radiopharmaceutical of the present embodiment can also be used as a therapeutic agent and an imaging agent in a diagnostic process or the like. As described above, the radioactive component of the present embodiment accumulates in a hypoxic area, and in particular, Cu-ATSM accumulates in cancer stem cells. Therefore, the radiopharmaceutical of the present embodiment is preferably a therapeutic agent used for treating tumors or an imaging agent used for imaging tumors. It is possible to produce the compound of the present embodiment in which a concentration of the radioactive component is as high as 200 MBq/mL or more, and in which a high radioactivity concentration is maintained by the production method of the present embodiment. Therefore, the compound of the present embodiment is suitable for therapeutic purposes in which therapeutic effects can be effectively exhibited due to a high radioactivity concentration. In particular, it is particularly preferable to use it as a therapeutic agent for tumors because of the above-mentioned property of accumulating in cancer stem cells.

The radioactive dithiosemicarbazone copper complex contained in the radioactive component of the present embodiment can accumulate on various tumors. Examples of tumors on which the radioactive dithiosemicarbazone copper complex accumulates include breast cancer, brain tumor, prostate cancer, pancreatic cancer, stomach cancer, lung cancer, colon cancer, rectal cancer, large bowel cancer, small intestine cancer, esophageal cancer, duodenal cancer, tongue cancer, pharyngeal cancer, salivary gland cancer, schwannoma, liver cancer, kidney cancer, bile duct cancer, endometrial cancer, cervical cancer, ovarian cancer, bladder cancer, skin cancer, hemangiomas, malignant lymphomas, malignant melanoma, thyroid cancer, parathyroid cancer, nasal cavity cancer, paranasal sinus cancer, bone tumor, hemangiofibromas, retinal sarcomas, penile cancer, testicular tumor, pediatric solid cancer, sarcoma, leukemia, or the like. These tumors may be primary or metastatic. The radiopharmaceutical of the present embodiment can be used for treating these tumors.

In addition, it is possible to use the radiopharmaceutical of the present embodiment by administering it in combination with other conventionally known drugs. For example, a chelating agent, which is administered in addition to the radiopharmaceutical of the present embodiment, for promoting excretion of radioactivity from an organ may be used in combination. Alternatively, an enema or the like for further promoting excretion of the radiopharmaceutical from an organ may be used in combination. Alternatively, an anti-angiogenic agent for enhancing an antitumor effect may be used in combination.

The radiopharmaceutical of the present embodiment can be provided in a form of a kit, to which other drugs are attached, for use in combination administration. For example, the radiopharmaceutical of the present embodiment may be in form of a kit obtained by combining the above-mentioned chelating agent, enema, metabolic inhibitor, or anti-angiogenic agent.

As described above, the embodiments of the present invention have been described, but the present invention is not limited to the above-described embodiments, and various changes can be made.

EXAMPLES

Hereinafter, the effects of the present invention will be made clearer by examples and comparative examples. The present invention is not limited to only the following examples but can be implemented with appropriate changes without departing from the scope of the invention.

Experimental Example 1

Various radical scavengers were added as stabilizing agents to $^{64}$Cu-ATSM, and effects of the various radical scavengers on stabilization of the $^{64}$Cu-ATSM were compared. A $^{64}$Cu-ATSM solution was prepared using a composition shown in Table 1. A concentration of $^{64}$Cu was 1.5 GBq/mL. A 0.2 mol/L glycine aqueous solution was prepared in advance. A $^{64}$Cu solution was prepared using this aqueous solution and was used for the reaction. In addition, ATSM was dissolved in dimethyl sulfoxide in advance to prepare a 0.5 mmol/LATSM dimethyl sulfoxide solution. This was mixed with the $^{64}$Cu solution, and thereby a $^{64}$Cu-ATSM solution was prepared.

Next, to this $^{64}$Cu-ATSM solution, respective compounds (radical scavengers) shown in Table 2 as candidates for stabilizing agents were added at a specified concentration. Three samples were prepared each time under each reaction condition while setting a total volume of each of the $^{64}$Cu-ATSM solution sample to 30 μL. A radiochemical purity of the $^{64}$Cu-ATSM was analyzed by a thin-layer chromatography immediately after the reaction, 5 hours from the reaction, and 24 hours from the reaction. Separation was performed with TLC Silica gel 60 (Merck) using methanol as a developing solvent. A percentage of $^{64}$Cu-ATSM that had not been decomposed was calculated (% Intact probe=amount of radioactivity of $^{64}$Cu-ATSM/total radioactivity×100).

TABLE 1

| Composition of drug | Per 1 mL |
|---|---|
| $^{64}$Cu | 3 MBq to 1.5 GBq |
| ATSM | 2.5 μg |
| Dimethyl sulfoxide | 0.02 mL |
| Glycine | 7.3 mg |
| Injection solvent | 0.98 mL |
| Stabilizing agent | * |

* Each candidate compound is added as a stabilizing agent at a specified concentration

TABLE 2

| Candidate compound for stabilizing agent | Test Example | Compound | Amount added |
|---|---|---|---|
| Acid-based | 1 | Ascorbic acid | 154.9 mg |
| | 2 | Citric acid monohydrate | 147 mg |
| | 3 | Citric anhydride | 85 mg |
| Amino acid-based | 4 | Methionine | 0.4 mg |
| | 5 | Cysteine hydrochloride monohydrate | 16.7 mg |
| Sodium salt-based | 6 | Sodium ascorbate | 4.4 mg |
| | 7 | Sodium thioglycolate | 3.3 mg |
| | 8 | Sodium bisulfite | 138.6 mg |
| | 9 | Sodium sulfite | 10 mg |
| | 10 | Sodium pyrosulfite | 12 mg |
| | 11 | Anhydrous sodium sulfite | 64.8 mg |
| Alcohol-based | 12 | Butylhydroxyanisole | 12.5 μg |
| | 13 | Mannitol | 89.6 mg |
| | 14 | Benzyl alcohol | 19.21 μL |
| | 15 | Ethanol | 133.3 mg |

Figure 2:
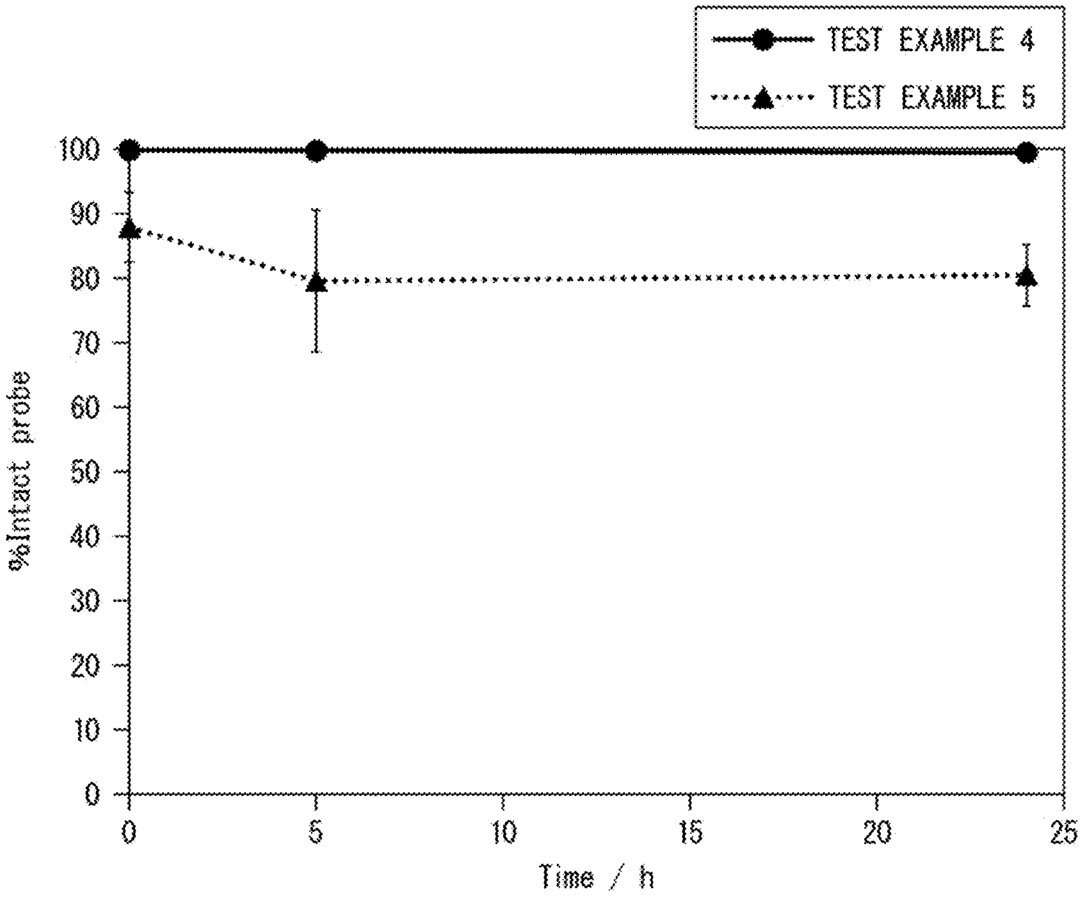
FIG. 2 is a graph showing a radiochemical purity of an amino acid-based candidate compound for a stabilizing agent on an hour basis in a present example.
Figure 3:
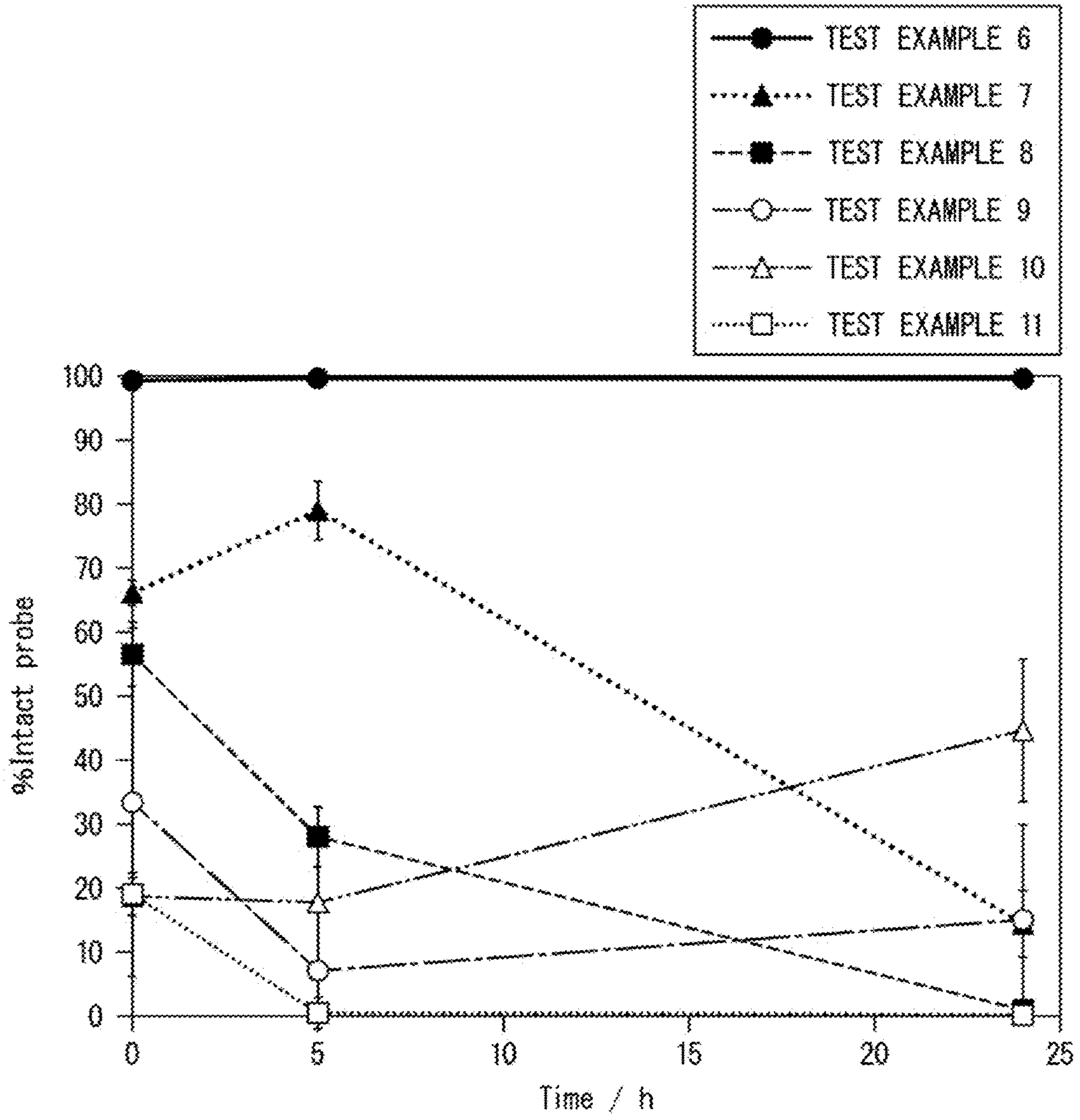
FIG. 3 is a graph showing a radiochemical purity of a sodium salt-based candidate compound for a stabilizing agent on an hour basis in a present example.
Figure 4:
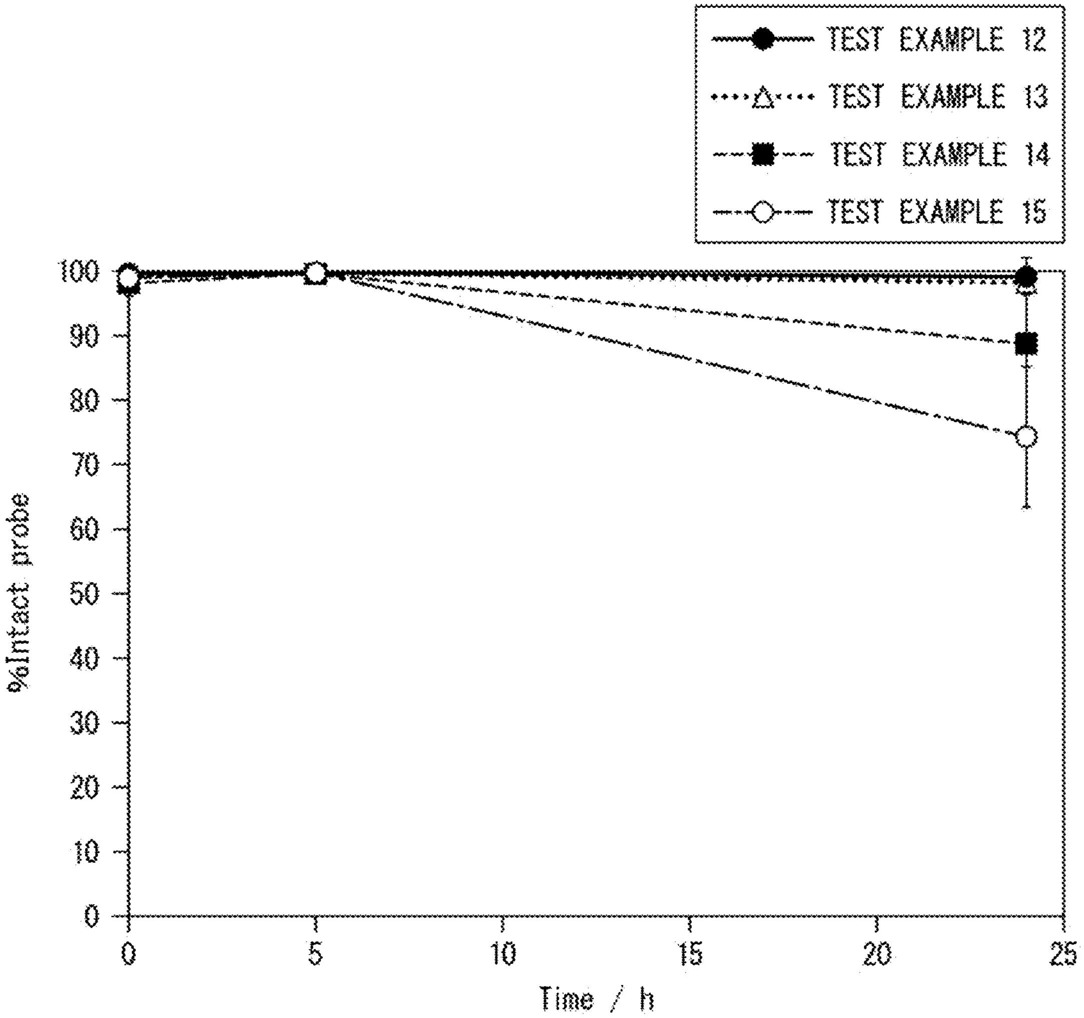
FIG. 4 is a graph showing a radiochemical purity of an alcohol-based candidate compound for a stabilizing agent on an hour basis in a present example.

As a result of the $^{64}$Cu-ATSM stabilizing effect by the addition of the respective test examples, a progress of % Intact probe on an hour basis is shown in FIGS. 1 to 4. FIG. 1 shows examination of acid-based candidate compounds (ascorbic acid, citric acid monohydrate, and citric anhydride). FIG. 2 shows examination of amino acid-based candidate compounds (methionine, and cysteine hydrochloride monohydrate). FIG. 3 shows examination of sodium salt-based candidate compounds (sodium ascorbate, sodium thioglycolate, sodium bisulfite, sodium sulfite, sodium pyrosulfite, and anhydrous sodium sulfite). FIG. 4 shows examination of alcohol-based candidate compounds (butylhydroxyanisole, mannitol, benzyl alcohol, and ethanol).

In addition, regarding 24 hours from the reaction, Table 3 shows an average of three samples of the respective test examples as AVR, and shows a standard deviation as SD.

TABLE 3

| Test Example | | 24 h % intact probe AVR | SD |
|---|---|---|---|
| 1 | L-ascorbic acid | 97.45 | ±1.33 |
| 2 | Sodium bisulfite | 0.98 | ±0.69 |
| 3 | Sodium sulfite | 15.07 | ±14.82 |
| 4 | Anhydrous sodium sulfite | 0.24 | ±0.09 |
| 5 | Citric acid monohydrate | 77.54 | ±10.62 |
| 6 | Citric anhydride | 74.64 | ± 9.31 |
| 7 | L-cysteine hydrochloride monohydrate | 80.46 | ± 4.79 |
| 8 | Sodium thioglycolate | 14.44 | ±5.20 |
| 9 | Sodium pyrosulfite | 44.65 | ±11.13 |
| 10 | Butyl hydroxyanisole | 99.09 | ±0.13 |

TABLE 3-continued

| Test Example | | 24 h % intact probe AVR | SD |
|---|---|---|---|
| 11 | L-methionine | 99.44 | ±0.12 |
| 12 | Benzyl alcohol | 88.72 | ±13.33 |
| 13 | Ethanol | 74.31 | ±10.91 |
| 14 | D-mannitol | 98.21 | ±1.81 |
| 15 | Sodium L-ascorbate | 99.58 | ±0.08 |

Based on the results of FIGS. 1 to 4, as compounds that can stably store the $^{64}$Cu-ATSM for up to 24 hours, 5 kinds were identified as follows: ascorbic acid of Test Example 1 (FIG. 1); methionine of Test Example 4 (FIG. 2); sodium ascorbate of Test Example 6 (FIG. 3); butylhydroxyanisole of Test Example 12 (FIG. 4); and mannitol of Test Example 13 (FIG. 4). As shown in Table 3, these compounds had % Intact probe of 97% or more after 24 hours. This shows that these compounds are stable because they were maintained in the form of the $^{64}$Cu-ATSM without being denatured even after 24 hours.

Experimental Example 2

Adsorbability of the $^{64}$Cu-ATSM was compared using a filter made of hydrophilic PES (manufactured by Merck Millipore, Millex GP, GP in the drawing) and a filter made of hydrophilic PVDF (manufactured by Merck Millipore, Millex GV, GV in the drawing) as sterilization filters used for filtration of the $^{64}$Cu-ATSM, in addition to a commonly used filter made of mixed cellulose ester (manufactured by Merck Millipore, Millex GS, GS in the drawing). A $^{64}$Cu-ATSM solution was prepared using a composition shown in Table 1. A concentration of $^{64}$Cu was 3 MBq/mL. A 0.2 mol/L glycine aqueous solution was prepared in advance. A $^{64}$Cu solution was prepared using this aqueous solution and was used for the reaction. In addition, ATSM was dissolved in dimethyl sulfoxide in advance to prepare a 0.5 mmol/L ATSM dimethyl sulfoxide solution. This was mixed with the $^{64}$Cu solution, and thereby a $^{64}$Cu-ATSM solution was prepared. To this solution, sodium ascorbate, mannitol, and ethanol were added as stabilizing agents at concentrations shown in Table 2. A total volume of each of the $^{64}$Cu-ATSM solution samples was 10.2 mL. An amount of radioactivity and a weight were measured immediately after the reaction. This sample was filtered with each of the filters (GS, GP, and GV), and then an amount of radioactivity and a weight were measured.

Figure 5:
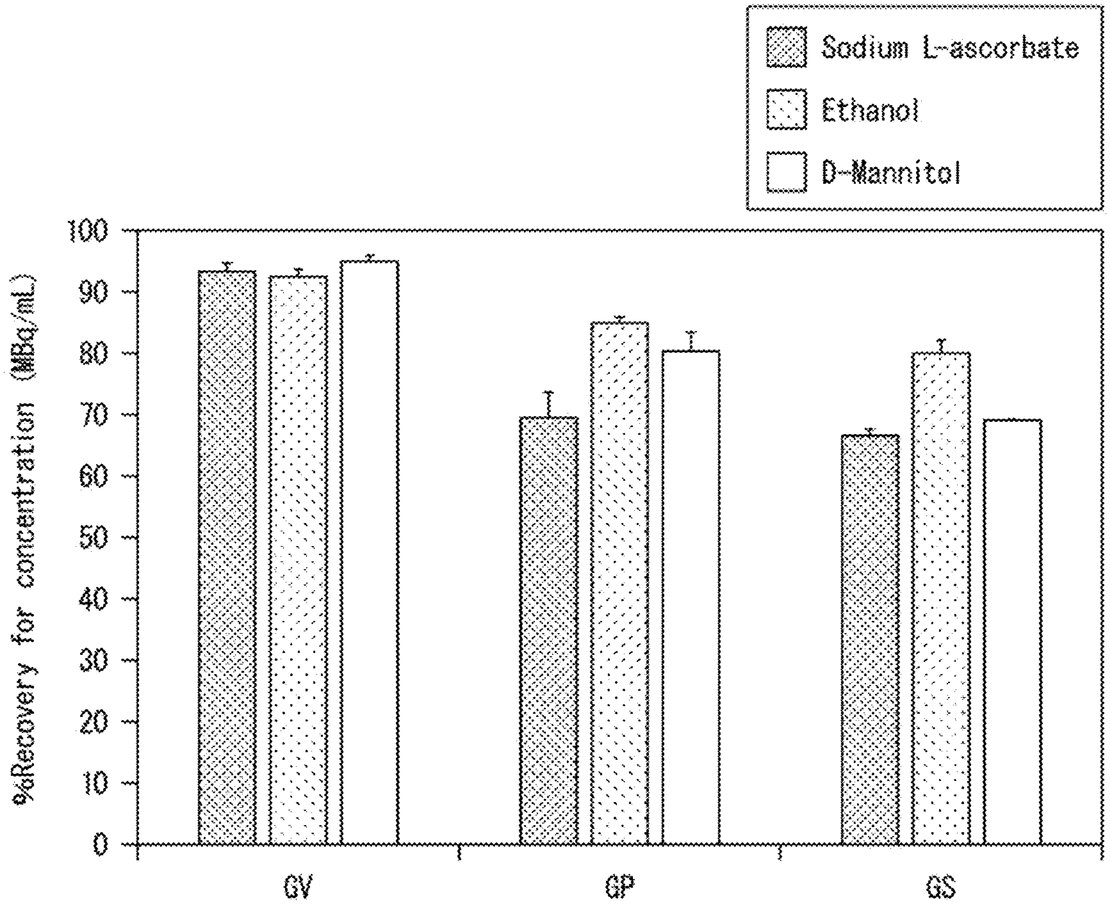
FIG. 5 is a graph showing a recovery percentage of filtration with various filters in a present example.
Figure 6:
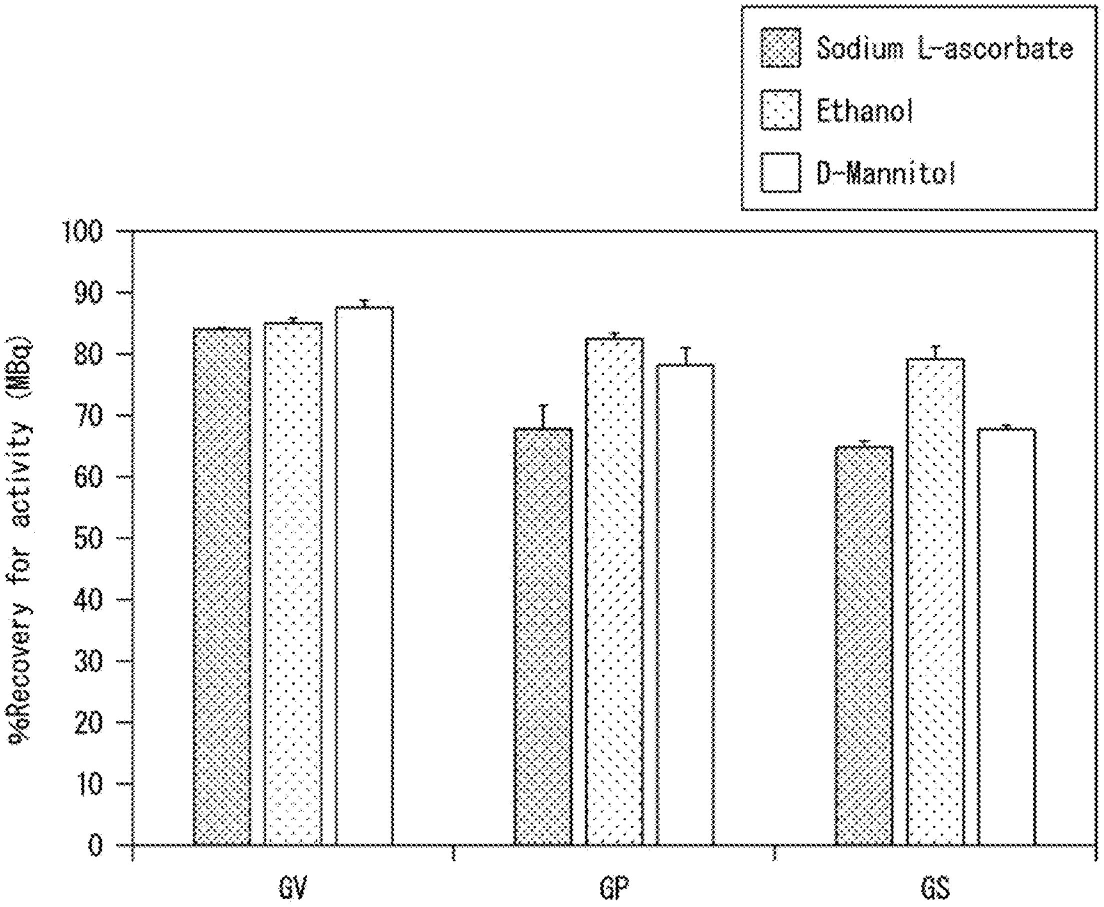
FIG. 6 is a graph showing a total recovery percentage of filtration with various filters in the present example.

This operation was performed on three samples each time under each condition using each of the filters. A recovery percentage (a percentage of a radioactivity concentration after recovery when a radioactivity concentration before recovery is defined as 100%), and a total recovery percentage (a percentage of an amount of radioactivity after recovery when an amount of radioactivity before recovery is defined as 100%) of the respective samples was calculated. A volume of the solution was calculated in terms of weight. FIG. 5 shows a recovery percentage in the respective stabilizing agents after filtration with various filters, and FIG. 6 shows a total recovery percentage. As a result, it was shown that an amount of adsorption was the smallest by filtering the $^{64}$Cu-ATSM using GV as a sterilization filter.

Experimental Example 3

A filter made of hydrophilic PVDF (manufactured by Merck Millipore, Millex GV, GV in the drawing) was employed as a sterilization filter used for filtration of the $^{64}$Cu-ATSM, and adsorbability of the $^{64}$Cu-ATSM at a high radioactivity concentration was checked. A $^{64}$Cu-ATSM solution was prepared using a composition shown in Table 1. A concentration of $^{64}$Cu was 1 GBq/mL. A 0.2 mol/L glycine aqueous solution was prepared in advance. A $^{64}$Cu solution was prepared using this aqueous solution and was used for the reaction. In addition, ATSM was dissolved in dimethyl sulfoxide in advance to prepare a 0.5 mmol/LATSM dimethyl sulfoxide solution. This was mixed with the $^{64}$Cu solution, and thereby a $^{64}$Cu-ATSM solution was prepared. To this solution, sodium ascorbate was added as a stabilizing agent at a concentration shown in Table 2. A total volume of the $^{64}$Cu-ATSM solution sample was 200 μL. An amount of radioactivity and a weight were measured immediately after the reaction. This sample was filtered with a filter, and then an amount of radioactivity and a weight were measured.

Figure 7:
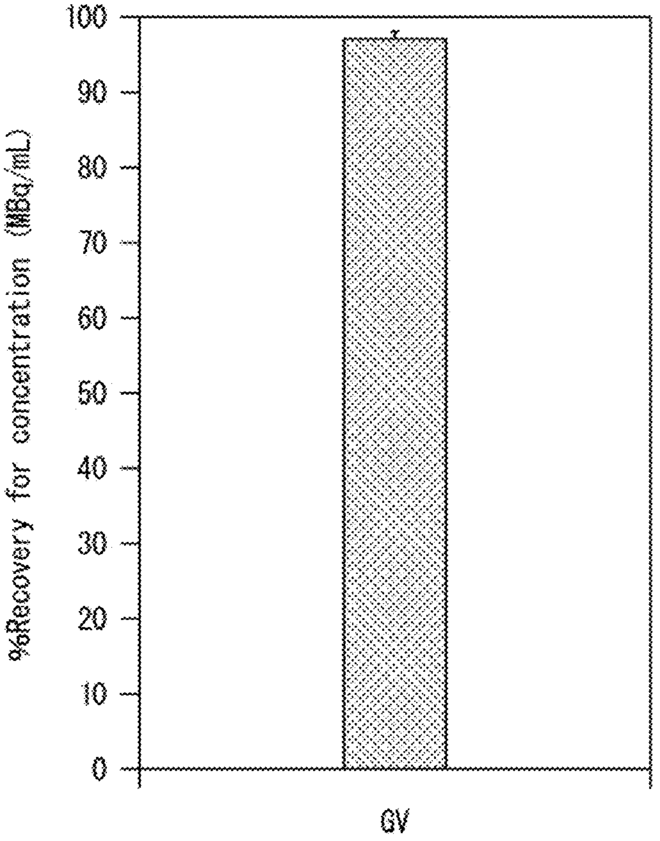
FIG. 7 is a graph showing a recovery percentage of filtration with a hydrophilic PVDF filter having a high concentration of radioactive components in a present example.
Figure 8:
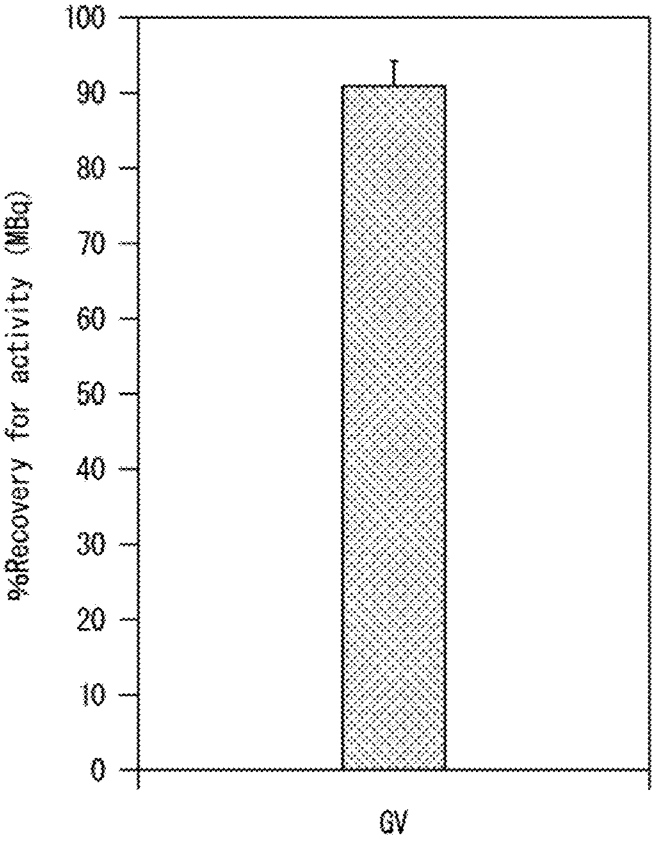
FIG. 8 is a graph showing a total recovery percentage of filtration with a hydrophilic PVDF filter having a high concentration of radioactive components in the present example.

This operation was performed on three samples each time. A recovery percentage (a percentage of a radioactivity concentration after recovery when a radioactivity concentration before recovery is defined as 100%), and a total recovery percentage (a percentage of an amount of radioactivity after recovery when an amount of radioactivity before recovery is defined as 100%) was calculated. A volume of the solution was calculated in terms of weight. FIG. 7 shows a recovery percentage after filtration with a filter, and FIG. 8 shows a total recovery percentage. As a result, it was shown that even the $^{64}$Cu-ATSM having a high radioactivity concentration used for therapeutic purposes was adsorbed less on the filter by filtering the $^{64}$Cu-ATSM using GV as a sterilization filter.

INDUSTRIAL APPLICABILITY

According to the method for producing a radiopharmaceutical and the radiopharmaceutical of the present invention, a method for producing a radiopharmaceutical and radiopharmaceutical are obtained, capable of maintaining a radioactive compound retaining a chemical structure and radioactivity at the time of production and after the production, and maintaining a usable period of a radiopharmaceutical. Accordingly, in the production and sale of the radiotherapeutic drug, Cu-ATSM, it is possible to use the method for producing a radiopharmaceutical and the radiopharmaceutical of the present invention for enlarging a delivery range by extending an expiration date, reducing cost by improving a production yield, reducing of exposure to workers, and the like.

The invention claimed is:

1. A method for producing a radiopharmaceutical that includes a radioactive component containing a radioactive dithiosemicarbazone copper complex represented by General Formula (1), the method comprising:

a stabilization step of adding a stabilizing agent containing at least one compound selected from the group consisting of ascorbic acid, methionine, sodium ascorbate, mannitol, and butylhydroxyanisole to a solution containing the radioactive component; and a filtration step of filtering the solution containing the radioactive component or a precursor thereof with a hydrophilic sterilization filter, wherein, in the radiopharmaceutical, a concentration of the radioactive component is 200 MBq/mL or more in terms of radioactivity concentrations;

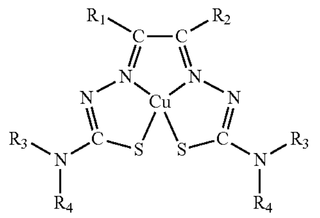
(1)

wherein in General Formula (1), $R_1$, $R_2$, $R_3$, and $R_4$ each independently represent a hydrogen atom, an alkyl group, or an alkoxy group; and Cu represents a radioactive isotope of copper; and wherein a percentage (%) Intact probe of the radioactive component that has not been decomposed at 24 hours after adding the stabilizing agent to the solution containing the radioactive component is 95% or more.

2. The method for producing a radiopharmaceutical according to claim 1, wherein, in the filtration step, a filter having hydrophilic polyvinylidene difluoride (PVDF) as a constituent material is used as the sterilization filter.

3. The method for producing a radiopharmaceutical according to claim 1 or 2, wherein, in the stabilization step, the stabilizing agent contains at least one compound selected from the group consisting of ascorbic acid, sodium ascorbate, and mannitol.

4. The method for producing a radiopharmaceutical according to claim 1, wherein, in the radiopharmaceutical, a concentration of the radioactive component is 1 GBq/mL or more in terms of radioactivity concentrations.

5. A radiopharmaceutical comprising:

a radioactive component containing a radioactive dithiosemicarbazone copper complex represented by General Formula (1); and a stabilizing agent containing at least one compound selected from the group consisting of ascorbic acid, methionine, sodium ascorbate, mannitol, and butylhydroxyanisole, wherein the radioactive component is fraction filtered with a hydrophilic sterilization filter, wherein a concentration of the radioactive component is 200 MBq/mL or more in terms of radioactivity concentrations, and

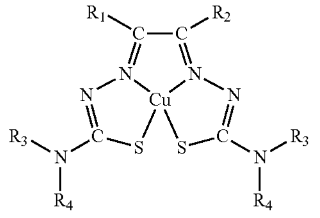
(1)

wherein in General Formula (1), $R_1$, $R_2$, $R_3$, and $R_4$ each independently represent a hydrogen atom, an alkyl group, or an alkoxy group; and Cu represents a radioactive isotope of copper, and wherein a percentage (%) Intact probe of the radioactive component that has not been decomposed at 24 hours after adding the stabilizing agent to the solution containing the radioactive component is 95% or more.

6. The radiopharmaceutical according to claim 5, wherein the stabilizing agent contains at least one compound selected from the group consisting of ascorbic acid, sodium ascorbate, and mannitol.

7. The radiopharmaceutical according to claim 5 or 6, wherein a concentration of the radioactive component is 1 GBq/mL or more in terms of radioactivity concentrations.

8. The radiopharmaceutical according to claim 5, wherein the fraction is fraction filtered with the sterilization filter having hydrophilic polyvinylidene difluoride (PVDF) as a constituent material.

9. The radiopharmaceutical according to claim 5, wherein the radiopharmaceutical is a therapeutic agent or an imaging agent for tumors.

10. The method for producing the radiopharmaceutical according to claim 1, wherein the stabilizing agent is butylhydroxyanisole.

11. The method for producing a radiopharmaceutical according to claim 1, wherein the stabilizing agent is ascorbic acid with an amount of 15.49 mg to 1.5 g per 1 mL of the radiopharmaceutical, wherein the stabilizing agent is sodium ascorbate with an amount of 0.44 mg to 44 mg per 1 mL of the radiopharmaceutical, or wherein the stabilizing agent is mannitol with an amount of 8.96 mg to 896 mg per 1 mL of the radiopharmaceutical.

12. The radiopharmaceutical according to claim 5, wherein the stabilizing agent is butylhydroxyanisole.

13. The radiopharmaceutical according to claim 5, wherein the stabilizing agent is ascorbic acid with an amount of 15.49 mg to 1.5 g per 1 mL of the radiopharmaceutical, wherein the stabilizing agent is sodium ascorbate with an amount of 0.44 mg to 44 mg per 1 mL of the radiopharmaceutical, or wherein the stabilizing agent is mannitol with an amount of 8.96 mg to 896 mg per 1 mL of the radiopharmaceutical.

* * * * *